United States Patent

Bisagni et al.

Patent Number: 4,966,971
Date of Patent: Oct. 30, 1990

[54] METHOD FOR PREPARING 1-CHLORO-5-ALKYLISOQUINOLINES CONDENSED WITH AROMATIC GROUPS

[75] Inventors: Emile R. B. Bisagni, Orsay; Marilys. Greletépouse Rautureau, Palaiseau, both of France

[73] Assignee: Centre National de la Recherche Scientifique (C.N.R.S.), Paris, France

[21] Appl. No.: 270,272

[22] Filed: Nov. 14, 1988

[30] Foreign Application Priority Data

Nov. 16, 1987 [FR] France .................. 87 15791

[51] Int. Cl.$^5$ .................. C07D 221/08; C07D 221/18; C07D 471/14; C07D 495/04
[52] U.S. Cl. ..................... 546/64; 546/70; 546/77; 546/79; 546/80; 546/101
[58] Field of Search ............ 546/64, 70, 77, 79, 546/80, 101

[56] References Cited

FOREIGN PATENT DOCUMENTS 0010029 9/1979 European Pat. Off. .
2422662 4/1977 France .

OTHER PUBLICATIONS

Croisy-Delcey et al., J. Org. Chem. vol. 53 (22) pp. 5301–5304 (1988).
LaMottina, J. Het. Chem., vol. 20 pp. 533–538 (1983).
Barton et al. J. Chem. Soc. Perkin Trans I, (5) pp. 503–507 (1976).
Lown et al., Can. J. Chem., vol. 48 (2) pp. 327–335 (1970).

Primary Examiner—Mukund J. Sham
Assistant Examiner—E. C. Ward
Attorney, Agent, or Firm—Bierman and Muserlian

[57] ABSTRACT

To prepare the compound (I), a lithiation of the compound (II) is performed, an aldehyde (IV) is reacted with the compound (III) formed, leading to the secondary alcohol (V) which is subjected to a reduction leading to the compound (VI), which is then subjected to a hydrolysis (of the dioxolane group)/cyclization/dehydration reaction. The procedure may be followed by a nucleophilic substitution reaction of the chlorine. The compounds (a) below exhibit antitumor activity.

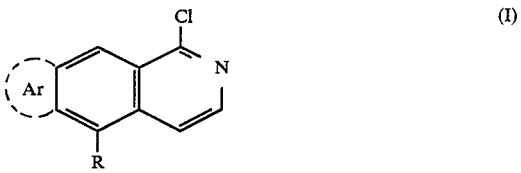
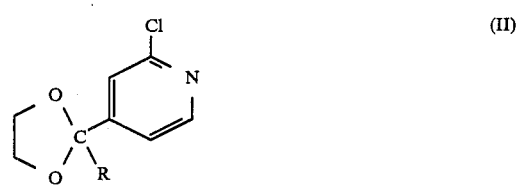
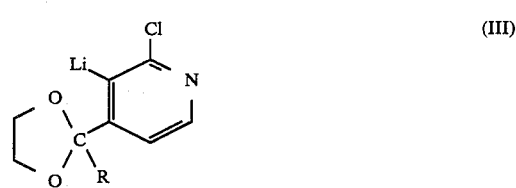
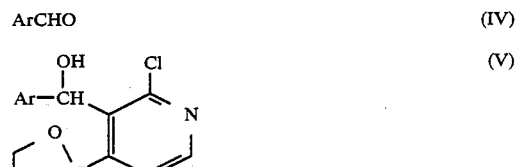
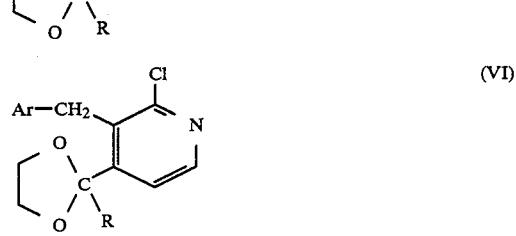
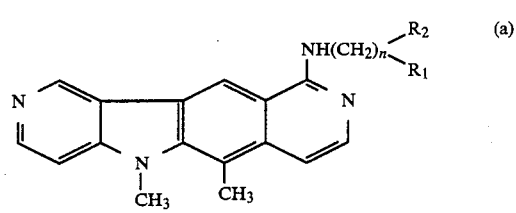
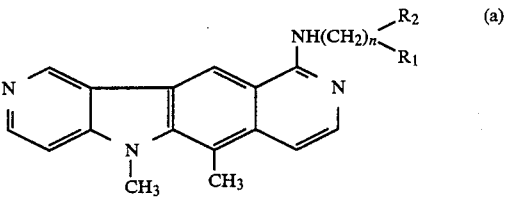

$R = C_1–C_3$ alkyl; Ar=aromatic or polycyclic aromatic group; $R_1$ and $r_2$=H or $C_1–C_3$ alkyl; and n=2 to 4. No drawing.

9 Claims, No Drawings

METHOD FOR PREPARING 1-CHLORO-5-ALKYLISOQUINOLINES CONDENSED WITH AROMATIC GROUPS

FIELD OF THE INVENTION

The present invention relates to a method for preparing 1-chloro-5-alkylisoquinolines condensed along their bond [g] with aromatic group, these isoquinolines being represented by the formula (I) below:

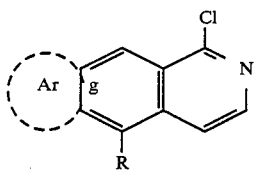

where
R denotes a $C_1$ to $C_3$ alkyl group: and
Ar denotes a mono- or polycyclic, aromatic or heteroaromatic group, optionally substituted, as well as the corresponding compounds obtained by nucleophilic substitution of the chlorine on the pyridine ring.

BACKGROUND OF THE ART

Some of these compounds are already known, there may be mentioned, in particular, compound (Ia):

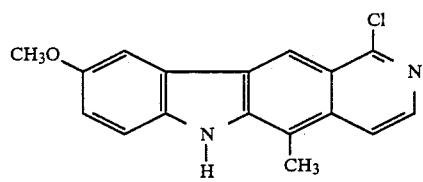

which is a synthesis intermediate for anticancer substances which are described in French Patent Application No. 2,436,786, and which is obtained by a complex method, since it comprises twelve stages, starting from:

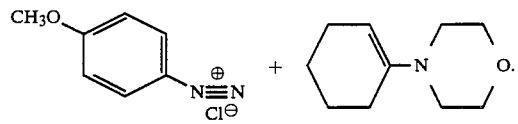

There may also be mentioned compound (Ib):

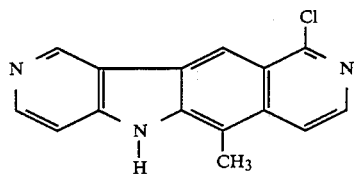

which is a synthesis intermediate for anticancer substances which are described in French Patent Application No. 2,387,229, and which is obtained in a low yield by an eleven-stage method starting from the compound:

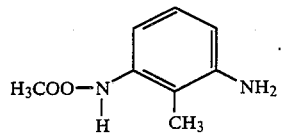

DETAILED DESCRIPTION OF THE INVENTION

The method according to the present invention involves only a limited number of stages, and it enables 1-chloro-5-alkylisoquinolines condensed with aromatic and heteroaromatic groups to be obtained in good yield.

This method essentially comprises the stages consisting in:

(a) performing a lithiation of the compound of formula (II):

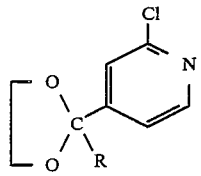

where R is as defined above, so as to form the compound of formula (III):

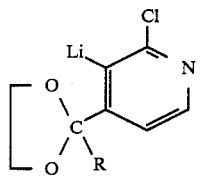

(b) reacting an aldehyde of formula (IV):

 ArCHO (IV)

where Ar is as defined above, with the abovementioned compound of formula (III), leading to the secondary alcohol of formula (V):

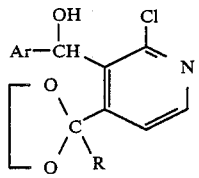

(c) the secondary alcohol of formula (V) is subjected to a reduction of the secondary alcohol group to a methylene group, leading to the compound of formula (VI):

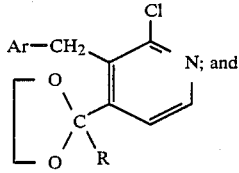

(d) the compound of formula (VI) is subjected to a hydrolysis (of the dioxolane group)/cyclization/dehydration reaction, leading to the compound of formula (I); and this procedure may be followed by a nucleophilic substitution reaction of the chlorine.

The compound of formula (II) is prepared according to the procedure described by J. L. Lamattina in "J. Het. Chem. 30 p. 533 (1983)" for 4-acetyl-2-chloropyridine ethylene glycol acetal (compound of formula (II) in which R denotes $CH_3$).

The stage (a) of lithiation of the compound of formula (II), leading to the compound of formula (III), is performed as for that of other pyridine derivatives, by the action of lithium diisopropylamide in anhydrous tetrahydrofuran at low temperature.

The stage (b) of the method of the present invention, namely the condensation with the aldehyde of formula (IV), is carried out in the traditional manner by addition of the latter to a solution, for example in anhydrous tetrahydrofuran, of the organolithium compound of formula (III).

It is possible to condense many substituted or unsubstituted aromatic and heteroaromatic aldehydes with the organolithium compound of formula (III), for example pyrrole or indole derivatives protected by groups such as alkyl, arylalkyl, alkyl- and arylsulfonyl or carbamoyl on their 1-vertex. Thus, there may be mentioned the application of this method to the preparation of compounds of formula (I) in which Ar denotes:

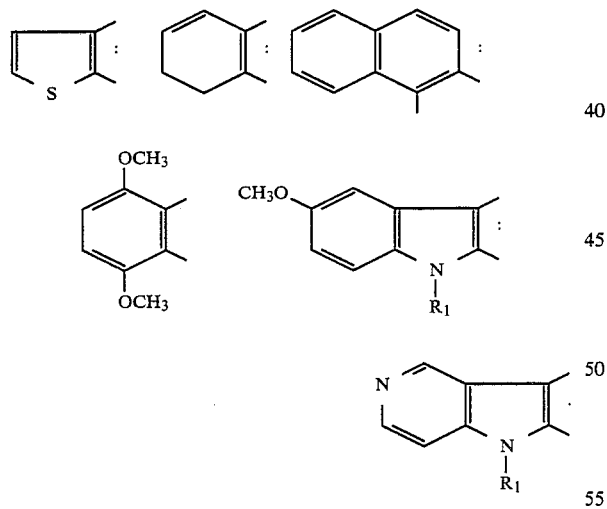

$R_1$ being as defined above.

The reduction of the secondary alcohol group to a methylene group, which is the reaction of the stage (c) of the method according to the present invention, may be performed by any known means for reducing benzhydrols, chosen in such a way that there is no reduction of the acetal group or removal of the chlorine on the pyridine ring. Triethylsilane dissolved in trifluoroacetic acid is suitable for this reduction.

The reaction of the stage (d) is a triple reaction which may be outlined as follows:

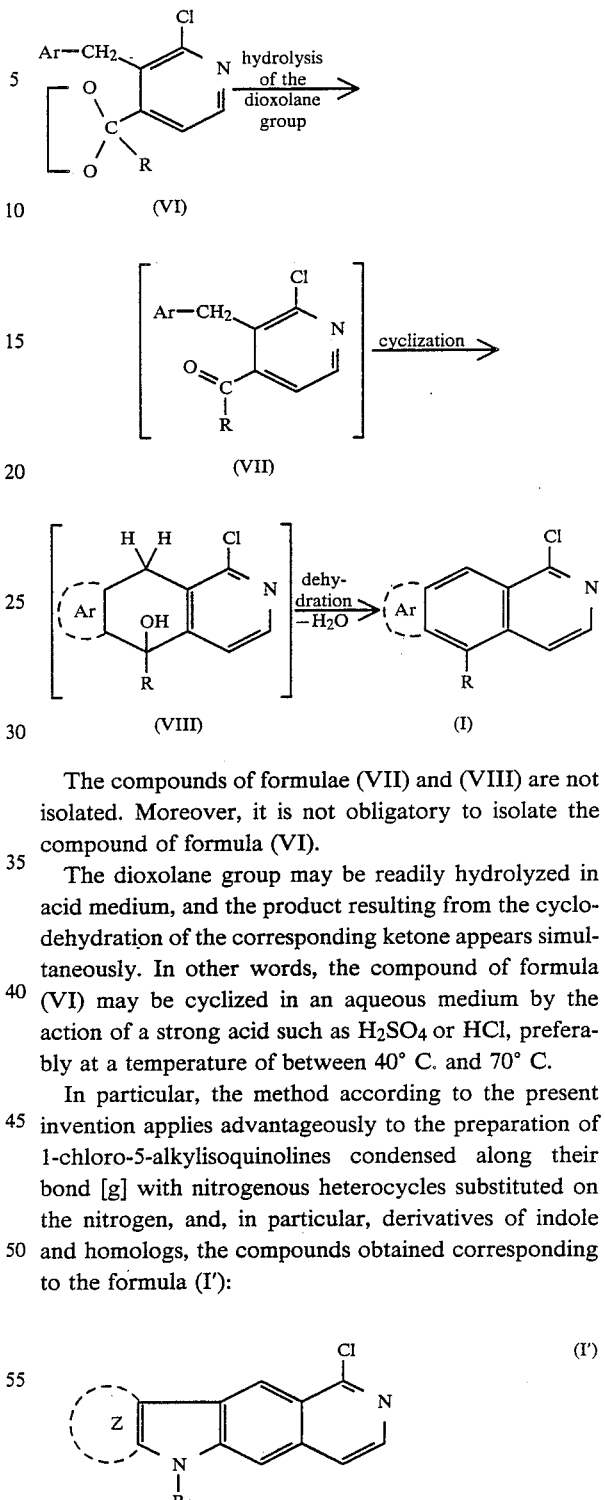

The compounds of formulae (VII) and (VIII) are not isolated. Moreover, it is not obligatory to isolate the compound of formula (VI).

The dioxolane group may be readily hydrolyzed in acid medium, and the product resulting from the cyclodehydration of the corresponding ketone appears simultaneously. In other words, the compound of formula (VI) may be cyclized in an aqueous medium by the action of a strong acid such as $H_2SO_4$ or HCl, preferably at a temperature of between 40° C. and 70° C.

In particular, the method according to the present invention applies advantageously to the preparation of 1-chloro-5-alkylisoquinolines condensed along their bond [g] with nitrogenous heterocycles substituted on the nitrogen, and, in particular, derivatives of indole and homologs, the compounds obtained corresponding to the formula (I'):

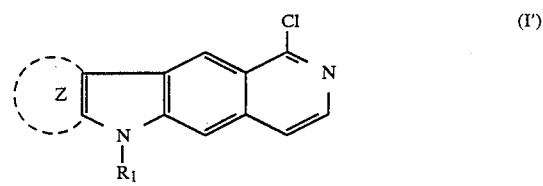

where:

R denotes a $C_1$ to $C_3$ alkyl group:

$R_1$ denotes a $C_1$ to $C_3$ alkyl group or a removable protective group; and

Z denotes a substituted or unsubstituted aromatic or heteroaromatic group, such as:

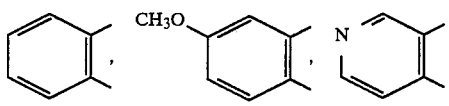

In this case, the N-protected aldehyde of formula (IVa):

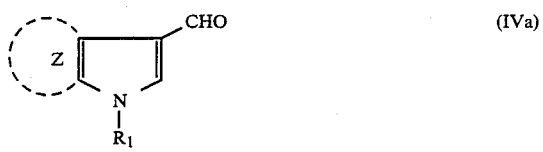   (IVa)

where $R_1$ is as defined above, is reacted as a compound of formula (IV).

The present invention also relates to the products obtained by carrying out this method and, by way of new products, the products of formula (I) in which Ar denotes:

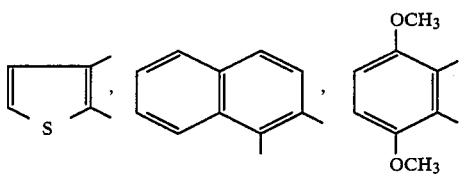

and in particular

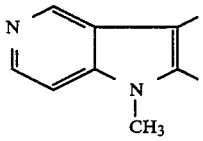

In particular, the products of formula

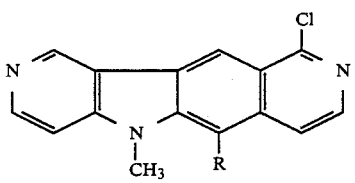

may lead by nucleophilic substitution of the chlorine on the pyridine ring to many compounds, for example to amines. There may thus be mentioned the compounds of formula:

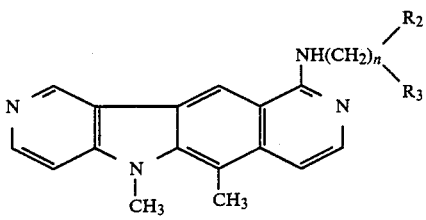

where:
n=2 to 4; and $R_2$ and $R_3$ each denote, independently of one another, H or $C_1$–$C_3$ alkyl.

These compounds, which are prepared by the action of the desired diamines on the corresponding chloro derivative obtained by the method of the invention, and obtained in the form of the free bases or of the corresponding pharmacologically acceptable salts (for example maleates or hydrochlorides), have an anticancer activity at least comparable to that of their homologs which are not alkylated on the indole nitrogen.

The present invention also relates to the therapeutic agents for the treatment of various cancers including leukemias, as well as to medicinal compositions containing them in combination with a pharmaceutically acceptable vehicle suitable for an intravenous or intraperitoneal administration of the compositions, such as physiological solution.

The doctor will determine the dosage of these therapeutic agents which will be most suitable. This dosage will vary according to the form of administration and the particular compound chosen and, moreover, it will vary with the particular patient subjected to the treatment. The compounds are useful in the same way as other similar agents, and the dosage level will be of the same order as for the latter.

In that which follows, examples of embodiment of the method of the invention for the production of new or previously described 1-chloro-5-methylisoquinolines condensed through their bond [g] with aromatic ring-systems will be described, as well as examples of preparation of some of their derivatives having pharmacological activity.

The melting points were taken on a Kofler stage. The $^1$H NMR spectra were recorded on a "Varian XL 100" apparatus, in the solvents indicated, and the chemical shifts are given in ppm relative to $(CH_3)_4Si$.

EXAMPLE 1

(a) First stage
Preparation of the dioxolane of 4-acetyl-2-chloropyridine:

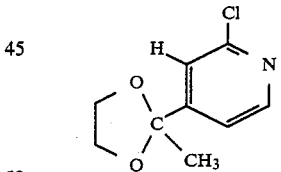

This compound was prepared as described by Lamattina J. L. in "J. Het. Chem. 1983, 20, 353", which describes it as a liquid. When distilled at 128° C. under 1333.22 Pa (10 mmHg), it crystallizes, giving a solid which melts at around 30° C.

(b) Second stage
Preparation of the three 4-acetyl-2-chloro-3-α-aryl-α-hydroxymethyl)pyridine ethylene glycol acetals:

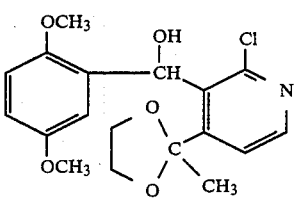   (A)

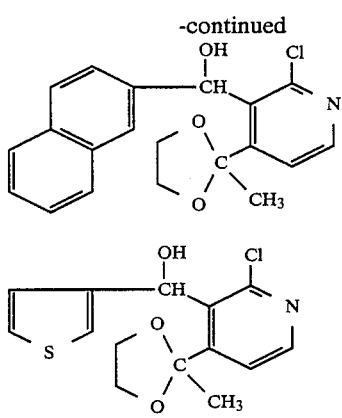

Tetrahydrofuran (THF, 50 ml), freshly distilled over a benzophenone+sodium mixture, is introduced into a 250-ml three-necked flask dried at 120° C. and maintained under argon. After the solvent has been cooled to 0° C., butyllithium (6.9 ml of a 1.6 M commercial solution, 11 mmol) and diisopropylamine (1.54 ml, 11 mmol), distilled over calcium hydride, are added successively. The mixture is stirred at 0° C. for 1 hour, and then cooled to −70° C. While cooling to this latter temperature is continued, the dioxolane obtained in the first stage (1.955 g, 10 mmol), dissolved in THF (10 ml), is then added dropwise. After 30 minutes following the completion of the addition, and the heterogeneous mixture is gradually converted to a gel. After 4 hours at −70° C., the chosen aldehyde (10 mmol), dissolved in THF (10 ml) is added dropwise, and the new mixture is stirred at the same temperature for 1 hour, and then left at room temperature for 15 hours. The mixture is poured into water and extracted with methylene chloride, and the combined organic phases are dried over sodium sulfate and evaporated. The oily residue gradually crystallizes in hexane or cyclohexane, and the solid obtained is recrystallized in the same solvent to yield the expected compound in the form of colorless crystals.

Acetal (A)
Yield: 72%
M.p. 92° C. (cyclohexane)
The elemental analysis of the acetal (A) thereby obtained gives the following results:

|  | C | H | N | Cl |
|---|---|---|---|---|
| Calculated for $C_{18}H_{20}ClNO_5$ | 59.10 | 5.51 | 3.83 | 9.69 |
| Found | 58.82 | 5.47 | 4.02 | 9.67 |

The nuclear magnetic resonance spectrum confirms the expected structure:
$^1$H NMR (CDCl$_3$) δ: 1.73 (s,3H,CH$_3$), 3.72 (s,2×3H,OCH$_3$), 3.8–4.0 (m,4H,CH$_2$CH$_2$), 4.29 (d,1H,OH,$J_{CH-OH}$=8.2Hz), 6.66–6.84 (m,4H,CHOH+3H-Ar) 7.57 (d, 1H,H-5 py,$J_{5-6}$=5Hz) 8.31 (d, 1H,H-6 py)

Acetal (B):
Yield: 73%
M.p. 146° C. (cyclohexane)
The elemental analysis of the acetal (B) thereby obtained gives the following results:

|  | C | H | N | Cl |
|---|---|---|---|---|
| Calculated for $C_{20}H_{18}ClNO_3$ | 67.51 | 5.10 | 3.94 | 9.96 |
| Found | 67.71 | 5.16 | 3.96 | 9.89 |

The nuclear magnetic resonance spectrum confirms the expected structure:
$^1$H NMR (CDCl$_3$) δ: 1.77 (s,3H,CH$_3$), 3.58–3.93 (m,4H,CH$_2$, CH$_2$, 4.35 (d,1H,OH,$J_{OH-CH}$=11.2Hz), 6.81 (d, 1H,CH-OH), 7.41–7.50 (m,5H,5H-Ar), 7.61 (d, 1H,H-5 py,$J_{5-6}$=5Hz), 7.78–7.87 (m,2H,2H-Ar), 8.41 (d,1H,H-6 py).

Acetal (C):
Yield: 61%
M.p. 105° C. (hexane)
The elemental analysis of the acetal (C) thereby obtained gives the following results:

|  | C | H | N | S | Cl |
|---|---|---|---|---|---|
| Calculated for $C_{14}H_{14}ClNO_3S$. 0.25H$_2$O | 53.16 | 4.58 | 4.43 | 10.12 | 11.23 |
| Found | 53.21 | 4.45 | 4.41 | 10.13 | 11.21 |

The nuclear magnetic resonance spectrum confirms the expected structure:
$^1$ NMR (CDCl$_3$) δ: 1.75 (s,3H,CH$_3$), 3.2–4.02 (m,4H,CH$_2$-CH$_2$), 4.52 (d, 1H,OH,$J_{OH-CH}$=11.5Hz), 6.62 (dd,1H,CHOH,$J_{CH-H-2th}$=2Hz), 6.88–7 (m,2H,H-2th+H-4th), 7.26–7.34 (m,1H,H-5th), 7.56 (d,1H,H-5 py,$J_{5-6}$=5 Hz), 8.37 (d,1H,H-6 py)

(c) Third stage:
Reduction/hydrolysis/cyclization of the acetals (A), (B) and (C) for the purpose of formation of the polycyclic derivatives according to the invention, of the respective formulae:

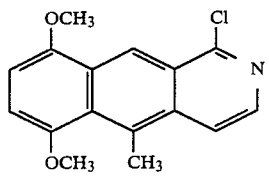
(IA)

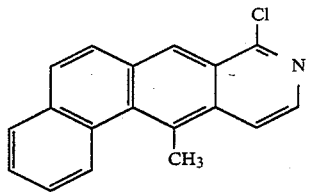
(IB)

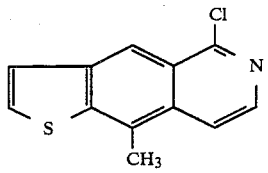
(IC)

The abovementioned compound (A) or (B) or (C) (1 mmol) is added to trifluoroacetic acid (2 ml), and triethylsilane (0.18 ml, 1.1 mmol) is added in a single portion to the resulting solution, stirred at a temperature of between 10° and 25° C. Stirring is continued for 18 hours at room temperature, and the excess trifluoroacetic acid is evaporated off under reduced pressure. 6N hydrochloric acid (20 ml) is added to the residue, and the mixture is stirred at 55°–60° C. for 4 hours to form the compounds (IA) and (IB), and only for 45 minutes to prepare the thienoisoquinoline (IC). The cooled mixture is alkalinized with ammonia solution and extracted with methylene chloride, and the organic phase, dried over sodium sulfate, is filtered and evaporated. The residue obtained crystallizes in the minimum amount of methanol (compounds IA and IC) or in hexane (compound IB), and the products obtained are recrystallized in the same solvent.

(IA): M.p. 170° C.; yield: 65%
(IB): M.p. 151° C.; yield: 37%
(IC): M.p. 138° C.; yield: 60%.

For the compounds (IB) and (IC), the melting points, the Rf values in TLC on silica plates, with several mixtures and solvents as eluents, and similarly the $^1$H NMR spectra are in all respects identical to those of the same products already described.

EXAMPLE 2

(a) First stage:
Preparation of 3-formyl-5-methoxy-1-methylindole:

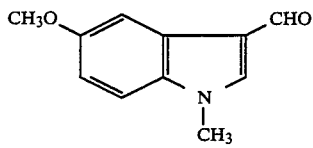

While cooling in order to maintain the temperature of the reaction medium below 15° C., phosphorus oxychloride (9 ml) is added dropwise to 35 ml of dimethylformamide (DMF), and 5-methoxy-1-methylindole (14.1 g), dissolved in DMF (25 ml) is added in a single portion. The resulting heterogeneous mixture is heated to 110° C. for 1 minute, and then maintained at 65° C. for 30 minutes while being stirred mechanically. After the mixture has been allowed to cool, it is decomposed by adding 200 ml of ice-cold water, and then treated with 5N sodium hydroxide solution (100 ml). The precipitate formed is filtered off and recrystallized in ethanol, to give 14.53 g (87.7%) of colorless scales, m.p.=134° C.

The elemental analysis of the product obtained gives the following results:

|  | C | H | N |
|---|---|---|---|
| Calculated for $C_{11}H_{11}NO_2$ | 69.82 | 5.86 | 7.40 |
| Found | 69.84 | 7.71 | 7.4 |

The nuclear magnetic resonance spectrum confirms the expected structure:

$^1$H NMR (CDCl$^3$) δ: 3.82+3.90 (2S,2×3H,N-CH3 +OCH3), 6.97 (q,1H,H-6,J$_{6-7}$=8.3 Hz,J$_{6-4}$=2.5Hz), 7.24 (d,1H,H-7), 7.80 (d,1H,H-4), 9.94 (s,1H,CHO).

(b) Second stage:
Preparation of 4-acetyl-2-chloro-3-[α-(5-methoxy-1-methyl-3-indolyl)-α-hydroxymethyl]pyridine ethylene glycol acetal.

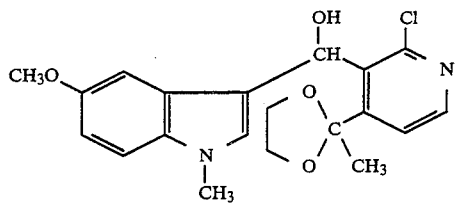

A 1.6N solution of butyllithium in hexane (15 ml 24 mmol) and diisopropylamine (3.36 ml, 24 mmol) are added successively to 100 ml of THF, cooled to 0° C. and maintained under dry argon. The mixture is stirred for 1 hour at 0° C. and cooled to −70° C., and 4-acetyl-2-chloropyridine ethylene glycol acetal (4 g, 20 mmol), dissolved in THF (10 ml), is added in a single portion. After 4 hours' stirring at −70° C., the aldehyde obtained in the first stage (3.78 g, 20 mmol), dissolved in THF (20 ml), is added gradually, and the mixture is stirred at −70° C. for 2 hours and then left at room temperature for 15 hours. The mixture is poured into water and extracted with methylene chloride, and evaporation of the solvent yields a residue which crystallizes slowly in ethyl acetate. The filtered solid recrystallizes in the same solvent, to give 5.04 g (65%) of colorless microcrystals, m.p. 125° C.

The elemental analysis of the product obtained gives the following results:

|  | C | H | N | Cl |
|---|---|---|---|---|
| Calculated for $C_{20}H_{21}ClN_2O_4$ | 61.78 | 5.44 | 7.21 | 9.12 |
| Found | 61.98 | 5.30 | 7.31 | 9.42 |

The nuclear magnetic resonance spectrum confirms the expected structure:

$^1$H NMR (CDCl$_3$) δ: 1.73 (s,3H,CH$_3$), 3.66 (s,3H,NCH$_3$), 3.58–3.95 (m,2×2H,CH$_2$CH$_2$), 3.85 (s,3H,OCH$_3$), 4.24 (d,1H,OH,J$_{OH-CH}$:11.6Hz), 6.39 (s,1H,H-2,Ar), 6.89 (m, 2H,CH-OH+H-6 Ar), 7.15–7.27 (m,2H,H-4 Ar+H-7 Ar), 7.60 (d,1H,H-5 py,J$_{5-6}$=5.3 Hz), 8.37 (d,1H,H-6 py).

(c) Third stage:
Preparation of 1-chloro-9-methoxy-5,6-dimethyl-H-pyrido[4,3-b]carbazole:

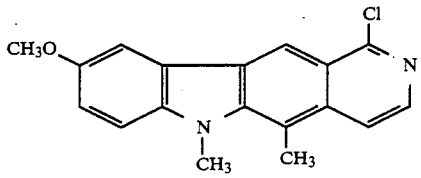

A mixture composed of the alcohol obtained in the stage (388 mg, 1 mmol), triethylsilane (0.18 ml , 1.1 mmol) and trifluoroacetic acid (2 ml) is stirred at room temperature for 20 hours, and evaporated to dryness. 5 ml of water and 5 ml of sulfuric acid (d=1.86) are added to the residue obtained, and the mixture is heated to 60° C. for 4 hours with stirring. After 15 hours at room temperature, 50 ml of water are added, and the mixture is alkalinized with concentrated ammonia solution and extracted with methylene chloride. Evaporation of the solvent yields a residue which crystallizes and recrystallizes in ethyl acetate, to give 170 mg (55%) of yellow microcrystals, m.p. 206° C.

The compound thereby obtained is identical to that described previously (m.p., analysis, NMR).

$^1$H NMR (CDCl$_3$) δ=3.07 (s,3H,CH$_3$-5), 3.99+4.13 (2s,2×3H,OCH$_3$+NCH$_3$), 7.28–7.38 (m, 2H, H-7+H-8), 7.72 (q,1H,H-10,J$_{10-8}$=2.5Hz,J$_{10-7}$=0.7Hz) 7.83 (q,1H,H-4,J$_{4-3}$=6.1Hz,J$_{4-11}$=1Hz), 8.21 (d,1H,H-3), 8.90 (d,1H,H-11).

EXAMPLE 3

(a) First stage:

Preparation of 3-formyl-1-methyl-1H-pyrrolo[3,2-c]-pyridine

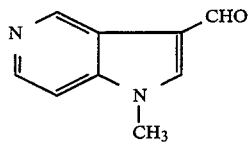

A mixture composed of 1-methyl-1H-pyrrolo[3,2-c]-pyridine (2.64 g, 20 mmol), hexamethylenetetramine (5.6 g, 40 mmol) and trifluoroacetic acid (35 ml) is heated under reflux for 3 hours. After the addition of 3N hydrochloric acid (100 ml), refluxing is continued for 3 hours, and the mixture is evaporated to dryness. The residue is taken up in water (75 ml) and alkalinized with N sodium hydroxide solution, and the resulting solution, saturated with sodium chloride, is extracted with methylene chloride. Evaporation of the solvent leaves a solid which recrystallizes in ethyl acetate, to yield 2.3 g (72%) of colorless needles, m.p. 109°–110° C.

Elemental analysis of the product obtained gives the following results:

|  | C | H | N |
|---|---|---|---|
| Calculated for C$_9$H$_8$N$_2$O | 67.50 | 5.00 | 17.50 |
| Found | 67.46 | 5.08 | 17.34 |

The nuclear magnetic resonance spectrum confirms the expected structure:

$^1$H NMR (CDCl$_3$) δ: 3.83 (s,3H,CH$_3$), 7.21 (q,1H,H-7,J$_{7-6}$=5.7Hz, J$_{4-7}$1Hz), 7.65 (s,1H,H-2), 8.42 (d,1H,H-6), 9.45 (d,1H,H-4), 9.93 (s,1H,CHO), (b) Second stage:

Preparation of 4-acetyl-2-chloro-3-[α-(1-methyl-1H-pyrrolo[3,2-c]pyrid-3'-yl)-α-hydroxymethyl]pyridine ethylene glycol acetal

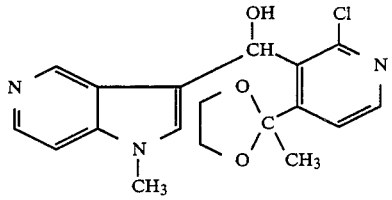

The reaction was carried out by applying the procedure described in the second stage of Example 2, with the aldehyde obtained in the first stage above (3.2 g, 20 mmol). After the treatment has been carried out as described, 4.24 g (59%) of colorless microcrystals, m.p. 150° C., have been formed.

The elemental analysis of the product obtained gives the following results:

|  | C | H | N | Cl |
|---|---|---|---|---|
| Calculated for C$_{18}$H$_{18}$ClN$_3$O$_3$ | 60.09 | 5.04 | 11.68 | 9.85 |
| Found | 59.92 | 5.22 | 11.62 | 9.84 |

The nuclear magnetic resonance spectrum confirms the expected structure: $^1$H NMR (CDCl$_3$) δ: 3.83 (s,3H,CH$_3$), 3.59–3.96 (m,2×2H,CH$_2$-CH$_2$), 3.72 (s,3H,NCH$_3$), 4.35 (broad s,1H,OH) 6.61 (s,1H,H-2 Ar), 6.82 (broad s,1H,CH-OH), 7.20 (d,1H,H-7 Ar,J$_{6-7}$=6Hz), 7.61 (d,1H,H-5 py,J$_{5-6}$=5.5 Hz), 8.33 (d,1H,H-6 Ar), 8.38 (d,1H,H-6 py), 8.81 (s,1H-H-4 Ar).

(c) Third stage:

Preparation of 10-chloro-5,6-dimethyl-5H-pyrido-[3'4':4,5]pyrrolo[2,3-g]isoquinoline:

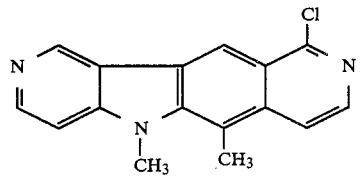

The compound obtained in the second stage (0.720 g, 2 mmol) is reduced, with stirring, at room temperature for 24 hours in trifluoroacetic acid (4 ml) in the presence of triethylsilane (0.64 ml, 4 mmol). The evaporation residue is then treated with 10 ml of water and 10 ml of sulfuric acid (d=1.86), at room temperature for 24 hours, with stirring. The reaction mixture is then treated as in the preceding example, to yield a solid which recrystallizes in ethyl acetate, giving 271 mg (48%) of pale yellow microcrystals of the expected compound, m.p. 256° C.

The elemental analysis of the product obtained gives the following results:

|  | C | H | N | Cl |
|---|---|---|---|---|
| Calculated for C$_{16}$H$_{12}$ClN$_3$ | 68.21 | 4.29 | 14.92 | 12.58 |
| Found | 67.93 | 4.23 | 14.98 | 12.51 |

The nuclear magnetic resonance spectrum confirms the expected structure:

$^1$H NMR ((CD$_3$)$_2$SO) δ: 3.14 (s,3H,CH$_3$-6), 4.03 (s,3H,NCH$_3$), 7.70 (q,1H,H-4,J$_{4-3}$=5.9Hz,J$_{4-1}$=0.6Hz), 8.14 (q,1H,H-7,J$_{7-8}$=6Hz,J$_{7-11}$=0.8Hz), 8.29 (d,1H,H-8), 8.66 (d,1H,H-3), 9.14 (broadened s, 1H,H-11), 9.63 (broadened s, 1H,H-1),

EXAMPLE 4

Application of the product obtained in Example 3 to the preparation of the following three compounds according to the invention:

(a) 10(3-Diethylamino-1-propyl)amino-5,6-dimethyl-5H-pyrido[3',4':4,5]pyrrolo[2,3-g]isoquinoline:

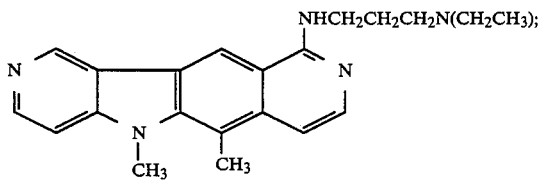

The compound obtained in the third stage of Example 3 (400 mg) is heated in excess (20 ml) 3-diethylaminopropylamine n an oil bath at 160° C. for 6 hours, and the excess diethylaminopropylamine is evaporated off under reduced pressure. The residue is taken up in water, alkalinized with N sodium hydroxide solution and extracted with methylene chloride. Evaporation of the solvent yields a residual oil, which gradually crystallizes in cyclohexane. The solid obtained recrystallizes in this solvent, giving 476 mg (89%) of crystals, corresponding to the hydrate of the expected compound, m.p. 149° C.

The elemental analysis of the product obtained gives the following results:

|  | C | H | N |
|---|---|---|---|
| Calculated for $C_{23}H_{29}N_5 \cdot H_2O$ | 70.23 | 7.89 | 17.81 |
| Found | 70.80 | 7.74 | 17.65 |

The nuclear magnetic resonance spectrum confirms the expected structure:

$^1$H NMR ((CD$_3$)$_2$SO): δ=1.02 (t,2×3H,(CH2CH3)2), 1.86 (m,2H,CH2-β), 2.45–2.66 (m,6H,(CH2CH3)2+CH2-γ) 2 99 (s,3H,CH3-6), 3.61 (m,2H,CH2-α), 4.17 (s,3H,NCH3), 7.14 (d,1H,H-7,J7-8=6.3Hz), 7.59 (broad s, 1H,NH), 7 62 (q,1H,H-4,J4-3=5.8Hz,J4-1=0.8Hz), 8.57 (d,1H,H-3), 9.01 (s,1H,H-11), 9.29 (d,1H,H-1).

The acid trimaleate of 10-(3-diethylamino-1-propyl)amino-5,6-dimethyl-5H-pyrido[3',4':4,5]pyrrolo-[2,3-g]isoquinoline (above compound) was then prepared:

This salt is obtained by pouring a solution of the above base (406 mg) in 50 ml of boiling acetone into a solution, also boiling, of 415 mg of maleic acid in 50 ml of the same solvent. The mixture is kept boiling for 1 minute and cooled, and the solid formed if filtered off to give 736 mg (94%) of microcrystals of the expected acid trimaleate, hydrated with 2 molecules of water, m.p. 193° C.

The elemental analysis of this salt gives the following results:

|  | C | H | N |
|---|---|---|---|
| Calculated for $C_{35}H_{41}N_5O_{12} \cdot 2H_2O$ | 55.33 | 5.93 | 9.22 |
| Found | 55.18 | 5.80 | 9.05 |

(b) 10-(3-Dimethylamino-1-propyl)amino-5,6-dimethyl-5H-pyrido[3',4':4,5]pyrrolo[2,3-g]isoquinoline:

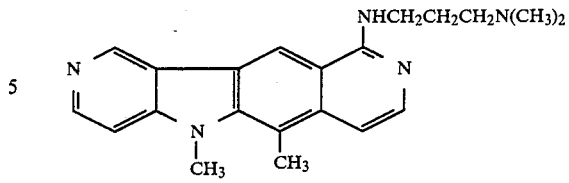

A mixture of the compound obtained in the third stage of Example 3 (2 g) and 3-diethylaminopropylamine (100 ml) is heated under reflux for 48 hours and treated as in section (a) above. The base, crystallized in cyclohexane, is converted to the acid trimaleate by treatment with an excess of maleic acid in acetone, and the filtered salt is treated with excess sodium hydroxide solution. After extraction with methylene chloride, the base recrystallizes in toluene, to give 1.14 g of crystals. The latter are reconverted as already described, to yield 2.16 g (43.8%) of the hydrate of the acid trimaleate of 10-(3-dimethylamino-1-propyl)amino-5,6-dimethyl-5H-pyrido[3',4':4,5]pyrrolo[2,3-g]isoquinoline.

The elemental analysis of the product obtained gives the following results:

|  | C | H | N |
|---|---|---|---|
| Calculated for $C_{33}H_{37}N_5O_{12} \cdot H_2O$ | 55.54 | 5.47 | 9.82 |
| Found | 55.60 | 5.43 | 9.89 |

The nuclear magnetic resonance spectrum confirms the expected structure:

$^1$H NMR (D$_2$)) δ: 2.4 (m,2H,CH2-β), 3.04 (s,2×3H,N(CH3)2), 3.07 (s,3H,CH3-6), 3.5 (m,2H,CH2-γ), 3.84 (t,2H,CH2-α), 4.3 (s,3H,NCH3-5), 6.07 (s,6H,CH=CH maleate), 7.55 (d,1H,H-7,J7-8=7.7Hz), 7.69 (d,1H,H-8), 8.05 (d,1H,H-4,J4-3=7Hz), 8 74 (d,1H,H-3), 9.15 (s,1H,H-11), 9.47 (s,1H,H-1).

(c) 10-(3-Ethylamino-1-propyl)amino-5,6-dimethyl-5H-pyrido[3',4':4,5]pyrrolo[2,3-g]isoquinoline:

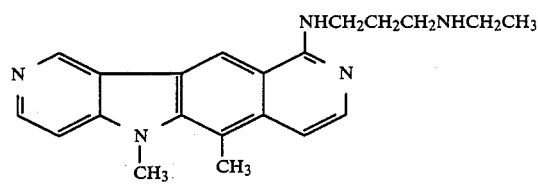

The compound obtained in the third stage of Example 3 (300 mg) is heated in an oil bath at 140° C. for 5 hours in 3-ethylaminopropylamine (15 ml), and the excess of the latter is evaporated off. The residue is taken up in water, alkalinized with N sodium hydroxide solution and extracted with methylene chloride. Evaporation of the solvent yields an oil, which is directly treated with an excess of maleic acid in boiling acetone. 560 mg (73.7%) of the hydrate of the acid trimaleate of 10-(3-ethylamino-1-propyl)amino-5,6-dimethyl-5H-pyrido-4':4,5]pyrrolo[2,3-g]isoquinoline, is thereby formed.

The m.p. of this product: melts gradually between 165° C. and 170° C.

The elemental analysis of this salt obtained gives the following results:

|  | C | H | N |
|---|---|---|---|
| Calculated for $C_{33}H_{37}N_5O_{12}\cdot H_2O$ | 55.54 | 5.47 | 9.82 |
| Found | 55.37 | 5.58 | 10.17 |

The nuclear magnetic resonance spectrum confirms the expected structure:

$^1$H NMR (D$_2$O) δ: 1.35 (t,3H,CH$_2$CH$_3$); 2.29 (m,2H,CH$_2$-β); 2.96 (s,3H,CH$_3$-6); 3.24 (m,2×2H,CH$_2$CH$_3$+CH$_2$-γ); 3.75 (t,2H,CH$_2$-α); 4.21 (s,3H,NCH$_3$); 6.11 (s,6H,CH=CH-maleate); 7.44 (d,1H,H-7,J$_{7-8}$=8Hz); 7.63 (d,1H,H-8); 7.90 (d,1H,H-4,J$_{4-3}$=6.9 Hz); 8.65 (d,1H,H-3); 8.94 (s,1H,H-11); 9.32 (s,1H, H-1).

The three compounds of Examples (4a), (4b) and (4c) above, obtained as described as well as in salt form, exhibit antitumor activity, the results of the pharmacological study of these substances in vitro and in vivo being described below:

1/ In vitro test

The method is that described by Paoletti et al. in "Chem. Biol Interaction 25, pages 45-58 (1979)". Increasing concentrations of the test compound are added to a cell culture of L 1210 leukemia line in the exponential growth phase. The culture is incubated at 37° C. in a CO$_2$ incubator, and the cells are counted every 24 hours. The calculation of the ID$_{50}$, the concentration of the product in micromoles per liter which 50% inhibits cell proliferation, is performed after 48 hours. The ID$_{50}$ of the compound of Example (4a) is 0.017 μM; of the compound of Example (4b) is 0.019 μM; and of the compound of Example (4c) is 0.033 μM.

By way of comparison, that of the compound unsubstituted on the indole nitrogen, described in French Patent Application No. 2,436,786, which is being studied in the clinical situation, is 0.018 μM.

2/ In vivo test

The method is that described by Geran et al. in "Cancer Chemother. 2 pages 7-57 (1972)".

All the male or female mice are inoculated intraperitoneally on day D$_0$ with a specified amount of viable tumor cells, the amount varying according to the tumor selected for the test.

The mice are then distributed in different batches. Each batch corresponding to the animals treated with the test product, at a given dose, is composed of 10 mice. The test product is dissolved in distilled water, and is administered intraperitoneally, for n days (D$_1$-D$_n$), varying according to the protocol selected, on the basis of 0.1 ml per 10 g of weight of the mice treated; the doses of the product administered are specified in the tables below.

The "negative control" batch, for which the animals are not treated with a product, comprises more than 2N animals, N being equal to the total number of mice treated with a product.

The antitumor activity is evaluated by considering the increase in the survival time of the treated animals compared with that of the animals of the "negative control" batch, according to the formula:

$$T/C = \frac{\text{with a dose of product}}{\text{median day of survival of the "negative control" animals}} \times 100$$

A compound is considered to be toxic when this value is equal to or less than 85%, or when the change in weight of the animals, expressed in grams and calculated by measuring the difference between the average weight of the batch measured on day 5 and the average weight of the same batch on day 1, is equal to or less than - 4 g.

The tests are performed with CD$_2$F$_1$ hybrid female mice, inoculated intraperitoneally with 10$^6$ P 388 strain leukemia cells. The test compound is administered either once (D$_1$), or for 5 days (D$_1$-D$_5$); the test product is compared with 5-fluorouracil (positive control), which is administered under the same conditions.

The number of surviving animals is evaluated on day D30. Under these conditions, a compound is considered to be active when the ratio T/C is greater than 128%.

The results are shown in the following tables:
Table I for the single administration at D$_1$
Table II for a repeated administration.

TABLE I

| PRODUCT | DOSE mg/kg | WEIGHT CHANGE W5-W1 (g) | MEDIAN DAY OF SURVIVAL | T/C % |
|---|---|---|---|---|
| Compound of Example (4c) in the form of the salt obtained | 2.5 | −1.8 | 13.8 | 118 |
|  | 5 | −0.8 | 14.0 | 121 |
|  | 10 | −0.2 | 14.1 | 122 |
|  | 20 | −1.2 | 15.2 | 131 |
|  | 40 | −2.3 | 16.0 | 138 |
|  | 80 | −4.3 | 8.1 | 70 |
| Compound of Example (4a) in the form of the salt obtained | 2.5 | −1.6 | 12.6 | 109 |
|  | 5 | −1.0 | 13.8 | 118 |
|  | 10 | −2.2 | 14.1 | 122 |
|  | 20 | −1.8 | 15.4 | 133 |
|  | 40 | −2.6 | 15.2 | 131 |
|  | 80 | −3.5 | 17.0 | 146 |
| 5-Fluorouracil | 200 | −2.2 | 16.0 | 138 |
| Distilled water |  | −0.9 | 11.6 |  |

TABLE II

| PRODUCT | DOSE mg/kg | WEIGHT CHANGE W5-W1 (g) | MEDIAN DAY OF SURVIVAL | T/C % |
|---|---|---|---|---|
| Compound of Example (4b) in the form of the salt obtained | 0.375 | +1.2 | 13.0 | 110 |
|  | 0.75 | +0.5 | 14.8 | 125 |
|  | 1.5 | +0.5 | 16.1 | 136 |
|  | 3 | −0.3 | 17.0 | 144 |
|  | 6 | +0.9 | 16.3 | 138 |
|  | 12 | −0.7 | 17.0 | 144 |
|  | 24 | −4.5 | 17.3 | 146 |
|  | 48 | −4.5 | 7.2 | 61 |
| 5-Fluorouracil | 20 | +1.0 | 20 | 169 |
| Distilled water |  | +2.6 | 11.8 |  |

What is claimed is:

1. A method for preparing a compound represented by the formula (I) below:

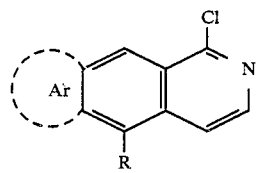

where:

R denotes a C$_1$ to C$_3$ alkyl group; and

Ar denotes a mono- or polycyclic, aromatic or heteroaromatic group, optionally substituted, which method comprises the stages consisting in:

(a) performing a lithiation by reaction of lithium diisopropylamide with the compound of formula (II)

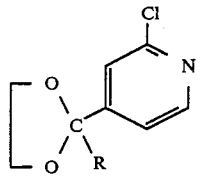  (II)

where R is as defined above, to form the compound of formula III

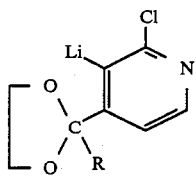  (III)

(b) reacting an aldehyde of formula IV

ArCHO  IV where Ar is as defined above, with a solution of the abovementioned compound of formula (III) leading to the secondary alcohol of formula (V)

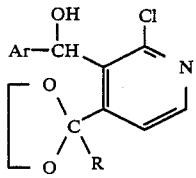  (V)

(c) the secondary alcohol of formula (V) is reacted with triethylsilane to reduce the secondary alcohol group to a methylene group, leading to the compound of formula (VI)

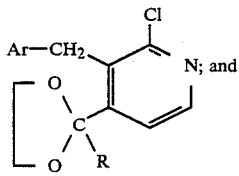  (VI)

(d) the compound of formula (VI) is subjected to an acid hydrolysis leading to the compound of formula (I).

2. The method as claimed in claim 1, wherein the stage (a) of lithiation of the compound of formula (II) is performed in anhydrous tetrahydrofuran.

3. The method as claimed in one of claim 1 wherein the stage (b) of condensation of the organolithium compound of formula (III) with the aldehyde of formula (IV) is performed by addition of the latter to a solution, in anhydrous tetrahydrofuran, of said organolithium compound of formula (III).

4. The method as claimed in one claim 1 wherein the reduction is performed with triethylsilane dissolved in trifluoroacetic acid.

5. The method as claimed in claim 1 in which the triple reaction of the stage (d) is performed in an aqueous medium by the action of a strong acid, at a temperature of between 40° C. and 70° C.

6. The method as claimed in claim 1, wherein the compound of formula (VI) is not isolated.

7. The method as claimed in claim 1, wherein compounds of formula (I) are prepared in which Ar denotes:

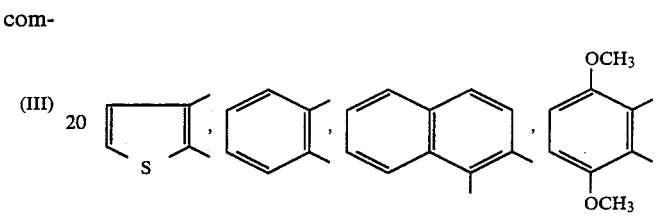

8. The method as claimed in claim 1, wherein compounds of formula (I')

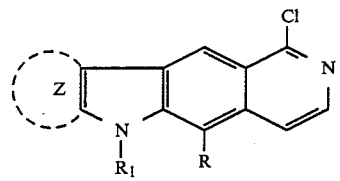  (I')

where:
R denotes a $C_1$ to $C_3$ alkyl group;
$R_1$ denotes a $C_1$–$C_3$ alkyl group or a removable protective group; and
Z denotes a substituted or unsubstituted aromatic or heteroaromatic group, such as:

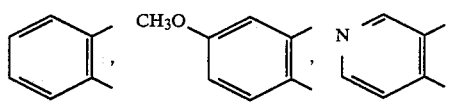

are prepared, in which case the N-protected aldehyde of formula (IVa):

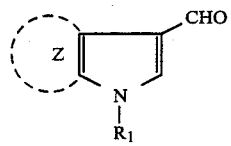  (IVa)

where $R_1$ is as defined above, is reacted as a compound of formula (IV).

9. The method as claimed in claim 1 wherein the product of stage (d) is subjected to a nucleophilic substitution reaction of the chlorine with 3-ethylaminopropylamine.

* * * * *